United States Patent
Battaglia et al.

(10) Patent No.: US 8,099,303 B1
(45) Date of Patent: *Jan. 17, 2012

(54) METHOD OF PROVIDING ENHANCED HEALTH CARE, FINANCE AND BENEFIT INFORMATION VIA A PERSONAL HEALTH FINANCE AND BENEFITS STATEMENT

(75) Inventors: Michael A. Battaglia, Louisville, KY (US); Christopher J. Nicholson, Louisville, KY (US); Jeanette R. Thomson, Louisville, KY (US); Matthew D. Reigle, Madison, NJ (US); Michael T. Antonetti, Louisville, KY (US); Darin A. Conn, Louisville, KY (US); Howard P. Shoaf, Louisville, KY (US)

(73) Assignee: Humana Inc., Louisville, KY (US)

( * ) Notice: Subject to any disclaimer, the term of this patent is extended or adjusted under 35 U.S.C. 154(b) by 1190 days.

This patent is subject to a terminal disclaimer.

(21) Appl. No.: 11/397,350

(22) Filed: Apr. 4, 2006

Related U.S. Application Data (60) Provisional application No. 60/668,152, filed on Apr. 4, 2005, provisional application No. 60/752,191, filed on Dec. 20, 2005.

(51) Int. Cl.
*G06Q 10/00* (2012.01)
*G06Q 50/00* (2012.01)
*A61B 5/00* (2006.01)
*G06F 19/00* (2011.01)

(52) U.S. Cl. ............................................. 705/3; 705/2
(58) Field of Classification Search .................. 705/2, 3, 705/4
See application file for complete search history.

(56) References Cited

U.S. PATENT DOCUMENTS

| | | | |
|---|---|---|---|
| 7,171,371 B2 * | 1/2007 | Goldstein | 705/2 |
| 7,444,291 B1 * | 10/2008 | Prasad et al. | 705/2 |
| 2005/0033609 A1 * | 2/2005 | Yang | 705/2 |
| 2006/0004612 A1 * | 1/2006 | Chewning et al. | 705/4 |
| 2006/0224443 A1 * | 10/2006 | Soza et al. | 705/14 |

* cited by examiner

*Primary Examiner* — Gerald J. O'Connor
*Assistant Examiner* — Neha Patel
(74) *Attorney, Agent, or Firm* — James C. Eaves, Jr.; Brian W. Chellgren; Greenebaum Doll & McDonald PLLC (57) ABSTRACT

The present invention relates to a method of providing enhanced health care, finance and benefit information via a personal health finance and benefit statement. Health statements may contain, for example, medical and pharmacy claim information, health care account information, and health related information for individuals. These statements may cover periods of time and can be provided by mail or electronically, and can be provided routinely or at the request of the individual.

11 Claims, 2 Drawing Sheets

METHOD OF PROVIDING ENHANCED HEALTH CARE, FINANCE AND BENEFIT INFORMATION VIA A PERSONAL HEALTH FINANCE AND BENEFITS STATEMENT

This application claims the benefit of the following two U.S. provisional patent applications: Ser. No. 60/668,152, filed Apr. 4, 2005; and 60/752,191, filed Dec. 20, 2005; both titled method of providing enhanced healthcare, finance and benefit information via a personal health finance and benefits statement. Both of these provisional applications are incorporated herein by reference.

BACKGROUND OF THE INVENTION

Field of the Invention

The present invention relates to a method of providing enhanced health care, finance and benefit information via a personal health finance and benefits statement. Depending on the plan or plans each member is in, each member's health statements may contain, for example, medical and pharmacy claim information, health care account information, and health related information for individuals. These statements may cover periods of time and can be provided by mail or electronically, and can be provided routinely or at the request of the individual.

SUMMARY OF THE INVENTION

The present invention relates to a method of providing enhanced health care, finance and benefit information so that the consumers of health care can make more informed decisions related to their health. Individuals who use health care services are often covered by insurance plans, which may cover some medical and pharmacy expenses. Some plans may only cover medical expenses. Other plans may only cover pharmacy expenses, such as a Medicare prescription drug plan. Other plans cover both. The individuals covered by these plans often decide which doctor or medical facility they will visit for services. In consultation with their medical providers, they receive prescriptions for various drugs and then must select the pharmacy to use to fill these prescriptions.

In addition to often having to make copayments to the medical provider for services and the pharmacy to fill their prescriptions, the users of health care insurance usually have an annual deductible which they must pay. Payment amounts will vary depending on the decisions made by the consumer. For example, it may cost the consumer more if they visit a medical professional not participating in the insurance network instead of a medical professional who does participate in the network. Visiting an urgent care center facility instead of an emergency room could result in different costs to the consumer. Having one drug prescribed instead of another drug and going to one pharmacy instead of a different pharmacy may result in different costs to the consumer.

In addition to the copayments and annual deductibles, the consumer may be managing a health care flexible spending account, a health savings account, or other health care account. Accounts like these may permit the user to use pre-tax dollars to pay copayments, coinsurance and annual deductibles, for services and tests not covered by their insurance, and to pay for over the counter health related items. Some of these accounts are "use or lose" accounts where all money in the account must be expended each year. Some of these accounts may allow for the account balance to roll over year to year.

Consumers of heath services also seek information about health services, generally having to research medical conditions or procedures at sources which may or may not be reliable. For example, consumers may conduct research on the Internet related to stopping smoking, losing weight, or breast or colon cancer.

It is the purpose of the present invention to provide the consumers of health care with reliable and accurate information about any or all of the following: their medical claims, pharmacy claims, dental claims, provider choices, drug choices, insurance choices and costs, account spending, cost-savings opportunities, plan benefit information, details about plan benefit function, notification of changes in physician or network or prescription drug coverage, and health related information. This is accomplished by providing a paper or electronic personal health finance and benefit statement. This statement can be provided periodically, for example quarterly or monthly, by the health care insurer. Alternatively, this statement can be provided at the request of the consumer. An additional option is to permit the consumer to tailor this statement as they desire, for example, requesting that they be provided only specific sections and specific information within those sections. The power of the statement is in its delivery of decision making guidance, related to cost and care decisions, driven at the line item or data element level. The statement will be designed to highlight to members the specific instance(s) in which they could have made an alternate decision and to educate them on how they could have made an alternative decision in order to encourage them to change their behavior. The statement recipient can retrospectively review their past decisions in order to more effectively plan and prepare for future health care situations.

More particularly, the present invention comprises a method for providing plan members with a personalized statement showing them useful information about their plan and the benefits they have received at least over the statement period. The method of providing to a plan member enhanced healthcare, finance and benefit information via a personal health finance and benefits statement comprises the following steps: a. maintaining data on at least one plan member; on that at least one plan member's benefits; and on at least one of that at least one plan member's medical claim data, prescription claim data, dental claim data, health-related account data, disease management program data, and information identified as of interest; b. extracting from the data maintained information needed to produce a personal health finance and benefits statement for at least one plan member; c. utilizing one of at least one statement templates to complete a statement for each of the at least one plan member for which information was extracted: (1.) inserting the extracted information appropriately into the statement template to reflect to that at least one plan member: (a.) numbers for that at least one plan member to watch which shows that member their plan year to date cost information in both a numerical and a graphical format; (b.) personal profile information about that at least one plan member and that at least one plan member's plan; and, (c.) information, by claim type, about each of that at least one plan member's claims processed during at least a period of time covered by the statement, including resolution of each claim, what that at least one plan member paid for each allowed claim, and what that at least one plan member's plan paid for each allowed claim; (2.) inserting into the statement template at least one marker with associated information related to the inserted extracted information to highlight that associated information to that at least one plan member; and (3.) inserting into the statement template healthcare information relevant to that at least one plan member; and, d. providing that at least one plan member with their completed statement.

In this method, the at least one marker can include one or all of a savings alert marker, a health alerts marker, a plan alert marker (how plan works, prescription coverage changes, network changes, or plan deadlines), a personalization marker, an online resources marker, or a phone resources marker.

Also, the healthcare information relevant to that at least one plan member inserted into the statement template can include information based on that at least one plan member's claims history, including, if desired, at least one coupon. Further, the healthcare information relevant to that at least one plan member inserted into the statement template can include information on topics requested by that at least one plan member.

The statement can be printed and distributed to the member by mail or similar service or the statement can be provided to the member electronically via a member portal on the Internet. The member could also be sent an electronic mail message notifying the member that the statement is available for viewing at the member portal.

Where a member's plan includes medical and pharmacy coverage, the method of providing to a plan member enhanced healthcare, finance and benefit information via a personal health finance and benefits statement can comprising the following steps: a. maintaining data on at least one plan member; on that at least one plan member's benefits; and on that at least one plan member's medical claim data, prescription claim data, health-related account data, disease management program data, and information identified as of interest; b. extracting from the data maintained information needed to produce a personal health finance and benefits statement for at least one plan member; c. utilizing one of at least one statement templates to complete a statement for each of the at least one plan member for which information was extracted: (1.) inserting the extracted information appropriately into the statement template to reflect to that at least one plan member: (a.) numbers for that at least one plan member to watch which shows that member their plan year to date cost information in both a numerical and a graphical format; (b.) personal profile information about that at least one plan member and that at least one plan member's plan including, in numerical and graphical format, any medical year to date co-payments for that member, any medical year to date in-network charges for that member; any medical year to date out-of-network charges for that member, any prescription year to date charges for that member; (c.) information about each of that at least one plan member's medical claims processed during at least a period of time covered by the statement, including resolution of each claim, what that at least one plan member paid for each allowed claim, and what that at least one plan member's plan paid for each allowed claim; (d.) information about each of that at least one plan member's prescription claims processed during at least the period of time covered by the statement, including resolution of each claim, what that at least one plan member paid for each allowed claim, and what that at least one plan member's plan paid for each allowed claim; (2.) inserting into the statement template at least one marker with associated information related to the inserted extracted information to highlight that associated information to that at least one plan member; (3.) inserting into the statement template a list of any communication that at least one plan member had with the plan provider; (4.) inserting into the statement template any health-related account information for that at least one plan member, including in numerical and graphical format account expenditure and balance information and including a list of any individual account activity plan year to date; (5.) inserting into the statement template healthcare information relevant to that at least one plan member; and, d. providing that at least one plan member with their completed statement. Additionally, the step of utilizing one of at least one statement templates to complete a statement for each of the at least one plan member for which information was extracted may include inserting into the statement template a personal healthcare record for that at least one plan member, the personal healthcare record including for a preceding year period a list, by date and provider, of any procedure provided or any drug and its dosage and quantity prescribed, and a list, by drug and dosage and quantity, of a number of times each drug was filled and the drug prescriber.

BRIEF DESCRIPTION OF THE DRAWINGS

A better understanding of the present invention will be had upon reference to the following description in conjunction with the accompanying drawings, wherein.

DETAILED DESCRIPTION OF THE PREFERRED EMBODIMENT

Figure 1:
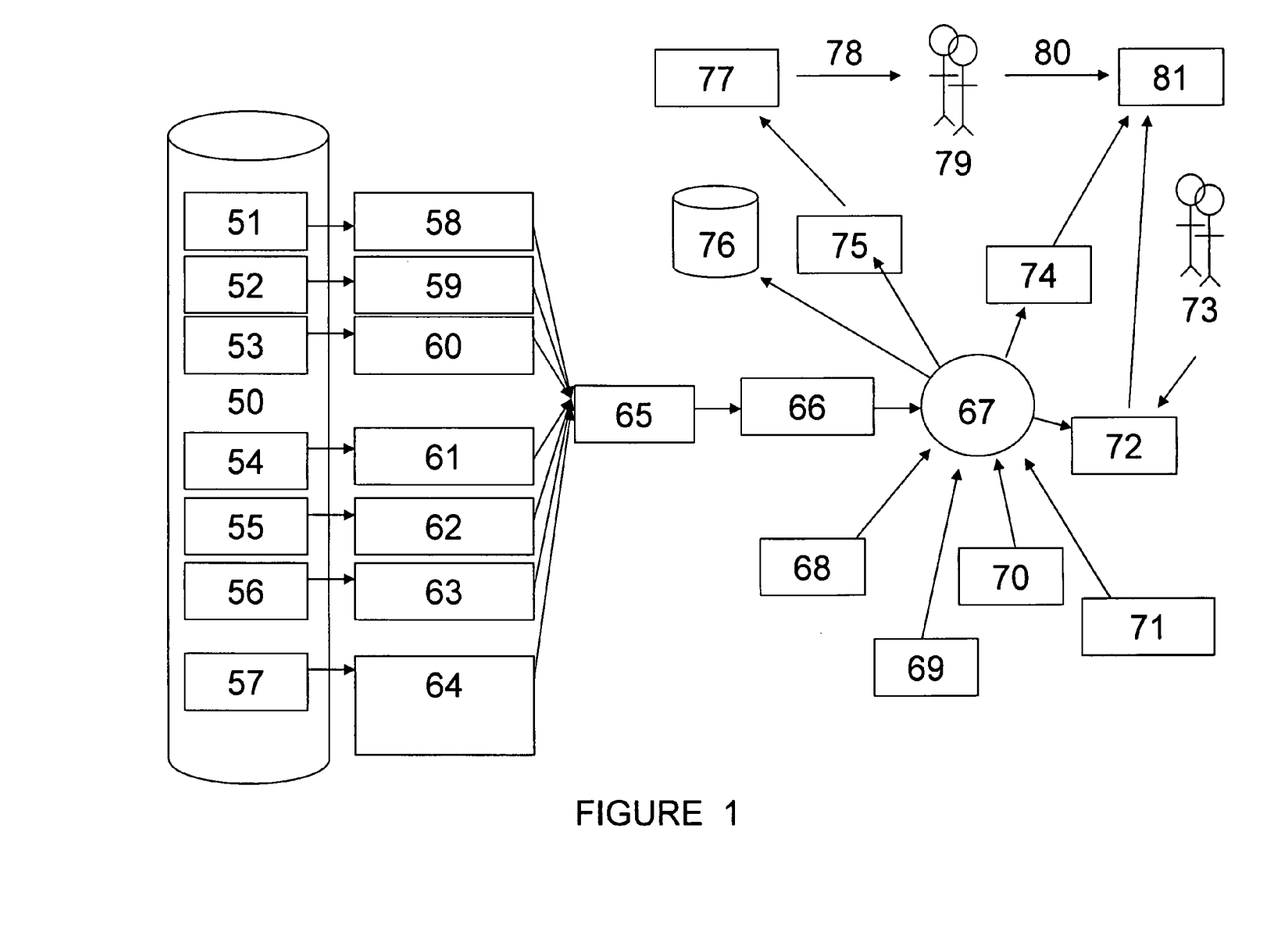
FIG. 1 demonstrates the architecture involved in obtaining information used and in producing the personal health finance and benefit statements; and, FIG. 2 shows a sample of the markers that can be used through the personal health finance and benefit statement.
Figure 2:
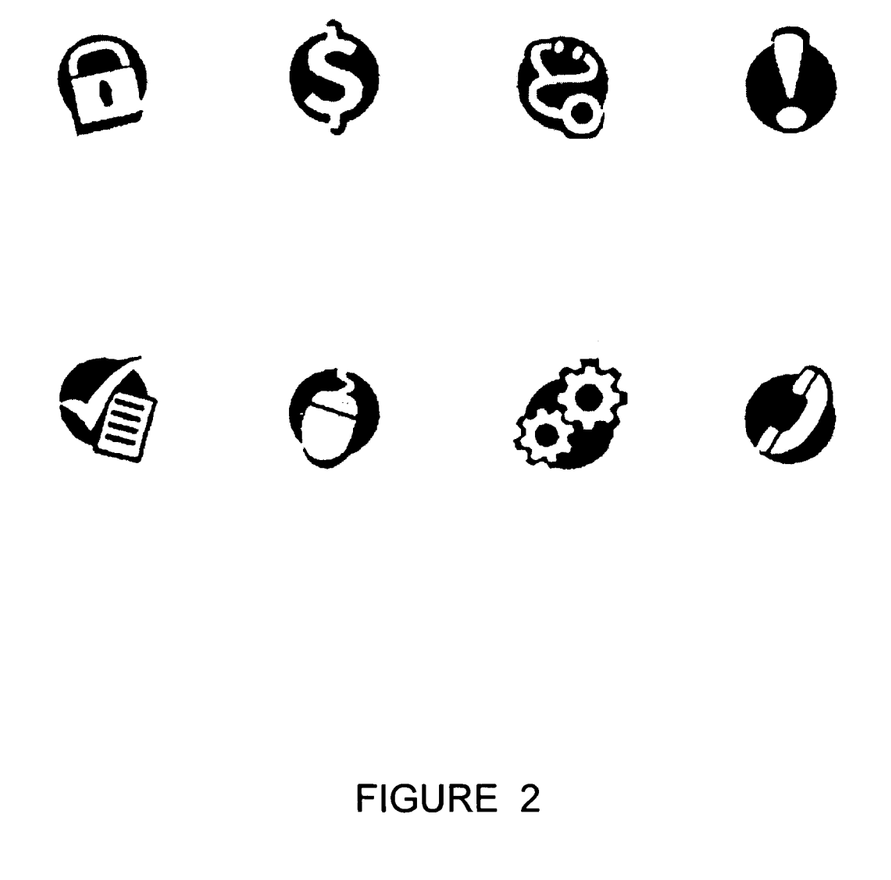

With reference to FIGS. 1 and 2, the method of providing enhanced health care information through the collection and processing of data to produce the personal health finance and benefit statement is shown and described. The statement produced uses information available to Humana Inc. (hereinafter Humana) from member data, processed medical and pharmacy claims, from spending accounts managed by Humana, third party providers, commercial groups and from other available information.

The architecture shown in FIG. 1 shows the data available in the Humana operational data store (ODS), a mineable data asset. The diagram displays data at a high level and may not represent all possible data that may be used to produce the statement. The following legend is used in FIG. 1: 50—Operational Data Storage (ODS); 51—Customers; 52—Members; 53—Benefits; 54—Medical claims; 55—Rx claims; 56—FSA/PCA/HSA/LAA Accounts; 57—Disease Management Programs; 58—Customer Extract; 59—Member Extract; 60—Benefits Extract; 61—Medical claims Extract; 62—Rx claims Extract; 63—Reimbursement Accounts Extract; 64—Disease Management Extract; 65—Composition Engine Input Assembly Process; 66—Composition Engine Input; 67—Composition Engine; 68—Statement Template; 69—Customer Supplied Content; 70—Images; 71—Personalized Content (Humana and/or 3rd Party); 72—Statement PDF; 73—Customer Service Representatives; 74—Statement HTML; 75—Printer; 76—Message Tracking; 77—Printed Personalized Statement; 78—Mailed to 79—Humana Members; 80—Views statement; and 81—Member Portal on Internet.

The data can be obtained or extracted from the ODS 50 on a periodic basis or on demand. Examples of data extracted from the ODS 50 or obtained from other sources are: identification of the member's insurance group; member identification information, including member identification number, member name and address information (member extract 59 from members data 52); information about the medical and pharmacy benefits to which the member is entitled (benefits extract 60 from benefits data 53); information about filed medical and pharmacy claims (medical claims 61 and pharmacy claims 62 extracts from medical claims 54 and pharmacy claims 55 data); information about the member's health account, including contributions and expenditures (reimbursement account extract 63 from FSA/PCA/HAS/LAA accounts data 56); information about any programs in which the member is enrolled (disease management extract 64 from disease management programs data 57); information about any medical category in which the member has expressed interest; information about any premiums received from the member's employer; and articles or content sourced from an external content provider.

Specific data extracts will be run to pull the data necessary for statement generation. The output of the data extracts will be assembled into a flat file by an assembly process. The flat file will be used by a composition engine to create the statement. The data extracts and assembly process will apply business rules and calculations to create additional data elements to drive personalization. For example, personal demographics may be compared against claims history to identify whether or not an age-, sex- or condition-based message should appear on the statement. This particular message may direct the member toward a specific procedure or behavior change. This kind of comparison may also determine the type of article or guidance-based content that appears on the statement. Additionally, current results may be compared to or displayed alongside the results of prior period results. For example, for account-based information, current health account balances may be compared to past account balances to demonstrate level of usage, remaining balances, account positions, etc. Once the resulting data is directed to the composition engine, additional rules, similar to the ones previously described, may be applied. The composition engine will consolidate the data with the statement template to produce the periodic statement. Because data will vary from member to member, the resulting statements will be unique for each member. The resulting statement will be available for print distribution or for display in an electronic environment as a .pdf file or other file type. The resulting member data may also be available to present in an html format on a website or other electronic delivery vehicle. The statements can be produced periodically as a batch process—for example, monthly, quarterly—or by plan year, or dynamically and upon request. The architecture of FIG. 1 shows further how Humana designs the statement layout and produces the statement.

An example of a personal health finance and benefit statement is described. The number of pages may vary from statement to statement. This example described has a cover page and a 9 page statement. The information presented in the statement will be customized to the member's profile, claims history, interests, or other personal characteristics. Thus, the sections appearing on each member's statement, the information contained within each section, the messages and captions that appear on the statement, and the order of the sections may vary from member to member. Also, the statement could be provided periodically, for example quarterly or monthly, or generated specifically as requested, or maintained current if posted on the Internet for member view there.

The statement described in this example is representative and presents one of many potential combinations of information and is a quarterly statement. The statement of the present invention may include any or all of the features described. These features and selected preferences may and will evolve over time as users will have the ability to modify these selections. For example, the statement described in this example describes a member enrolled in a PPO which has both medical and prescription coverage. Similar statements could be produced for members in just a medical plan, or just a prescription plan such as, for example, one of the new Medicare prescription drug plans where only pharmacy claims information would be provided in the statement.

The initial cover page of the statement identifies the member and the information contained in the statement. An example cover page includes identification that this is Humana's SmartSummary, a personal health finance and benefits statement. The cover page could include: the statement period (Jan. 1, 2005 to Mar. 31, 2005), the member id (999999999), the member name (Ruth-Anne Elizabeth Boyd), and this member's network (Humana/ChoiceCare Network PPO), all identified at the upper right of this initial cover page. The member's name and mailing information are at the lower left or at a location needed for mailing.

A welcome note is provided at the left column. This welcome note would preferably change from statement to statement. An example welcome note is: "Welcome to your personal health finance and benefit statement. We know that health care decisions can be complex and you often don't have all the information you need to feel confident when you're using your health benefits. This statement represents a new approach to showing you information about your health care expenses, at both a detailed and summary level so you can see the real impact on your budget each year. We welcome your input as we strive to continually be a trusted source of health information for our members."

An indication of what this quarterly statement contains is displayed in the column to the right on this cover page. An example is: "What's inside . . . . Numbers for you to watch, page 1, current amounts left of your deductibles, payment accounts, and service quotas. The value of your health plan, page 1, Dollar totals of your savings and advantages of membership so far this plan year. Your personal profile of benefits, page 2, Your plan details with current amounts used and other options you've selected. Overview of your insurance claims, page 3, At-a-glance listing of all your medical and prescription claims this quarter. Calls you made to Humana, page 4, A list of calls you made this quarter to customer service. Your health care accounts, page 5, Detailed summary of how you've used your FSA to pay for health care this quarter. What's new in health care?, page 6, Article briefs on new treatments, research, and the latest trend in health care services. Your personal health care record, page 8, Portable 12-month review of medical services you've received and prescriptions you take."

With that table of contents shown in the "What's inside" portion, the member can easily turn to the appropriate page to view the desired information. Now we provide examples of information that is in the 9 page statement following this cover sheet.

An example page 1 of 9 of the statement: The currency of the information is provided, as in "The information in this statement is current as of Mar. 31, 2005." Next, there is a section titled "Numbers for you to watch", which was listed in the What's inside listing on the cover page. That "Numbers for you to watch" section could read:

|  | Amount remaining | |
| --- | --- | --- |
|  | Left to pay | Left to use |
| Coverage First Allowance Available | — | 0 |
| Before you meet your deductible (in-network) | $347.20 | — |
| Before you reach the maximum out of your pocket limit (in-network) | $347.20 | — |
| In your Flexible Spending Account |  | $554.93 |
| Of covered physical therapy visits | — | 16 |

This "Numbers to watch" section identifies current amounts the member has left to pay toward the deductible, information about the balances the member has in payment accounts such as a flexible spending account or personal care account, and any service quote information. This section may also include information regarding other health related limits associated with the plan, for example, covered physical therapy visits. These current balances can help the member know whether or not they have money or other balances left for a service. All of these numbers are cumulative numbers for the member's plan year.

Certain markers are used throughout this statement to get the reader's attention. Examples are shown in FIG. 2 and described later. However, a "$" marker can be included in this "Numbers for you to watch" section which tells the reader to see page 7 to learn more about current health trends.

Following the "Numbers for you to watch" section at the top of page 1, a section titled "The costs and value of your plan" follows. An example of this section is:

The costs and value of your plan (as of Mar. 31, 2005) "Negotiated savings" shown here are for network charges only, which have been negotiated for you as a Humana member. In addition to what you paid with your plan, you may also be responsible for changes billed but not currently covered by your plan.

| Out of your pocket | | | | |
| --- | --- | --- | --- | --- |
|  |  | What you saved | | |
|  | Total billed charges | Negotiated savings | What Humana paid | What you paid |
| Medical | $3,538.00 | $2,070.20 | $500.00 | $967.80 |
| Prescriptions | $387.43 | — | $118.36 | $269.07 |
| Total | $3,925.43 | $2,070.20 | $618.36 | $1,236.87 |

These "out of your pocket" numbers are plan year cumulative. A "$" marker can also be included stating: Your savings this quarter were $2,688.56, 68% of this quarter's total health care costs. Additionally, a simple bar graph can be provided which has a column for "what you saved" ($2,688.56) and a column for "what you paid" ($1,236.87).

| From your paycheck | | | |
| --- | --- | --- | --- |
|  | Total | What your employer pays | What you paid |
| Premiums | $2,310.00 | $1,980.00 | $330.00 |

These numbers are plan year cumulative. Further, in addition to these numbers, a simple line graph showing the what the employer paid ($1,980) and what the member paid ($330) can be provided to give a visual impression of the employer vs. employee contribution amounts in addition to just listing the numbers. Again, a "$" marker can be included to explain to the member "If you maintain this coverage type throughout the year, your employer will pay a total of $9,240.00 of 85% of the cost of your premiums . . ."

This costs and value of the member's plan section is designed to pull together information and present it in a way that it can be absorbed by the viewer in a single glance. The value of the member's plan section sums the dollar amounts of the member's medical and prescription claims total charges, the dollar amount that Humana defrayed for the member's health care through network discounts, the dollar amount that Humana paid in payment of claims, and the total amount the member paid out of pocket, all shown in four columns that can be viewed in one line. This section can show the member what they are paying for their health care plan and their medical and pharmacy claims, what their employer is paying for the member's health care plan, what their total charges are for medical and pharmacy claims, identify the Humana discount and the amount paid by Humana. This section shows the member not only how much they have paid for their medical plan and claims, it identifies the benefits they are receiving from their employer and from Humana. In this example shown, the member is shown that their employer is paying 84% of the member's health care insurance premiums.

Following this plan cost section in the middle of page 1, a listing of the markers used throughout the statement and what they represent can be provided at the bottom of page 1 in a section titled "Look for these markers throughout your statement". Also, these sample markers are shown in FIG. 2.

Under a subsection titled "Decision opportunities", three markers are shown and described. The "$" marker represents: Savings alerts: Opportunities for you to save money next time. See pages 3, 6 and 7 inside. The "stethoscope" marker represents: Health alerts: Tips for maintaining or improving your health in the future. See page 7 inside. The "meshing gears" marker represents: How your plan works: Information about how your plan applies to your specific services.

The "Health plan alerts" subsection is represented by the "!" marker and includes: Prescription coverage changes: Notice of upcoming changes to copays or coverage for medications you take. See page 4 inside. It also includes: Network changes: Physician or facilities changing network status. It also includes: Plan deadlines: Reminders of dates to submit information or take action.

The "Options to select" subsection can include the following 3 markers: A "checklist" marker represents: Personalization: Opportunities for you to set preferences for your statement and other communications and services. A "computer mouse" marker represents: Online Resources: Web tools to help you get what you need when you need it. See page 2 and 8 inside. A "telephone handset" marker represents: Phone Resources: Phone tools to help you get what you need when you need it.

Any other desired markers can be used, as these symbols are examples only. Any symbol can be used for these defined markers and additional markers can be included for highlighting other areas for the member. For example, a "lock" marker can be used to identify information related to privacy of information.

Savings Alerts and Prescription Coverage Change messages let members know about options to save money that include information specific to the member, like the name of a prescription drug they are taking that has a coupon alternative or the precise dollar amount of the copay they pay/would pay for each alternative suggested in the message. Tier change notification messages include the current dollar amount of the copay for that drug for that member as well as the dollar amount of the new copay.

Health alerts are triggered by information specific to a member (like age, gender, claims history of using a certain drug or not having a certain type of test or procedure within a given timeframe) to suggest options they might consider about future health care that are relevant to that member at that point in time.

An example page 2 of 9 of the statement, which includes the "Your personal profile of benefits" section:

Your personal profile
About you
Member name Ruth-Anne Elizabeth Boyd
Member ID: 999999999
Your plan year: Jan. 1, 2005 to Dec. 31, 2005
Your medical plan: Coverage First, Single
Your prescription plan: RxImpact w/Rollover
Lifetime maximum $5,000,000
Your network: Humana/ChoiceCare Network PPO

| Your accounts | |
|---|---|
| X | Flexible Spending Account |
| X | Coverage First Account |
| X | Rx Impact Account |
| Your eligible programs | |
| X | Personal Nurse |
| X | Disease Management |
| — | Health Risk Assessment |
| — | Non-Smoking Benefit |
| — | Wellness Points Program |
| Partnership opportunities | |
| X | Email your statement |
| X | Register at myhumana.com |
| — | Electronic EOBs |

The member is enrolled in or is eligible to enroll in those items identified with an X and not in those identified with a _. As this member does not receive electronic explanation of benefits documents, a "computer mouse" marker can be included here which states: To choose another way for us to communicate with you, register or log on to MyHumana, your password-protected personal home page on.www.humana.com.

| Your medical benefits | |
|---|---|
| Copays for | Primary care/Specialist |
| Office visits | $25.00/$40.00 |
| In-network charges | |
| Coverage First Allowance | $500.00 |
| Deductible | $1,250.00 |
| Percent Humana Pays (coinsurance) | 100% |
| Max out of your pocket | $1,250.00 a year |
| Out-of-network charges | |
| Deductible | $2,500.00 |
| Percent you pay (coinsurance) | 30% |

| -continued | |
|---|---|
| Percent Humana pays (coinsurance) | 70% |
| Max out of your pocket | $5,000.00 a year |
| Your prescription benefits | |
| Allowances Humana pays per prescription | |
| In-network/Out-of-Network | With Rollover |
| Group A Drugs | $30 |
| Group B Drugs | $20 |
| Group C Drugs | $10 |
| Group D Drugs | $5 |
| Maximum amount per prescription/year | |
| Groups A, B, C | up to $75/$1,000 |
| Group D | up to $250/No maximum |

These numbers in the "Your medical benefits" section are static and are plan dependant. In addition to these static numbers, a "What you've spent" section can be included which provides numerical and graphical representations of the plan year cumulative numbers for this member.

For example, adjacent the office visit copay information, the fact that this member has paid $65 worth of copays to date for the plan year can be stated and a horizontal bar graph can show this amount against the annual limit, which for this plan is unlimited.

Adjacent the In-network charges information, the fact that this member has used the Coverage First Allowance of $500 and has coinsurance of $902.80 to date for the plan year can be stated and a horizontal bar graph can proportionally show the member how this $500 allowance and coinsurance of $902.80 relate to the $1,250 deductible.

Similar numbers and graph can be provided adjacent the Out of network charges information. In this example, there are no out of network charges to date for this plan year for this member, so $0 deductible and $0 coinsurance would be listed and graphed against a $2,500 deductible and a $5,000 maximum out of pocket.

In the "Your prescription benefits" section, adjacent the Humana allowances and the maximum amount per prescription/year sections, dollar totals and horizontal graphs are again provided. For example, as is explained later, to date this plan year, Humana has paid $118.36 for this member's prescriptions. That dollar amount is listed and graphically represented. Also, as is explained later, to date for this member's prescriptions, this member has paid $269.07 for Group A, B, and C prescriptions and $0 for Group D prescriptions. Those dollar amounts are listed and graphically represented.

An example page 3 of 9 of the statement, which details the medical claims received during the statement period: Medical claims we received (Jan. 1 to Mar. 31, 2005) This section lists new claims that occurred this quarter or adjusted claims from last quarter. Processing health care claims involves collecting information from many sources and adjusting it to specific plan agreements. If you have a question about information listed in this section, you can call the customer service number listed at the bottom of this page. If you believe a claim was processed incorrectly, you will need to submit a written "grievance and appeal".

Jan. 5, 2005, claim 123456789012346

Coverage First Allowance $332.00
Carol Jones, MD (Out-of-Network)
Screening Infection

| | |
|---|---|
| Total Charge | 571.00 |
| Humana discounts | 120.00 |
| Humana exclusions | 94.00 |
| What you paid with this plan | |
| Copay/Deductible/Coinsurance | 25.00/—/— |
| Humana Paid | 332.00 |

A "$" marker can be included with this claim, which states: Humana negotiates lower rates for you with their in-network physicians, and your plan covers more of the costs for in-network services. You can see a list of in-network physicians by using the Physician Finder tool at www.humana.com.

Jan. 19, 2005, claim 123456789012348

Coverage First Allowance $168.00
Jefferson County Ambulance (In-network)
Transport, Acute Respiratory

| | |
|---|---|
| Total Charge | 536.00 |
| Humana discounts | 280.00 |
| Humana exclusions | 70.00 |
| What you paid with this plan | |
| Copay/Deductible/Coinsurance | —/18.00/— |
| Humana Paid | 168.00 |

Jan 19, 2005, Claim 123456789012349
St. Jude Hospital (In-network)
Emergency Room Acute Respiratory

| | |
|---|---|
| Total Charge | 689.00 |
| Humana discounts | 425.00 |
| Humana exclusions | 79.20 |
| What you paid with this plan | |
| Copay/Deductible/Coinsurance | —/184.80/— |
| Humana Paid | — |

Jan. 19, 2005, Claim 123456789012351
St. Jude Hospital (In-network)
Acute Respiratory - Inpatient Bed Stay

| | |
|---|---|
| Total Charge | 1,110.00 |
| Humana discounts | 525.00 |
| Humana exclusions | 195.00 |
| What you paid with this plan | |
| Copay/Deductible/Coinsurance | —/390.00/— |
| Humana Paid | — |

Venous Blood Draw

Total Charge 18.00 NOT ALLOWED This procedure is not allowed separately, as it is part of a more global code. We relied on internal criteria to make this determination.

Depo-Medrol Injection Suspension 80 mg/ml

| | |
|---|---|
| Total Charge | 95.00 |
| Humana discounts | — |
| Humana exclusions | 58.00 |
| What you paid with this plan | |
| Copay/Deductible/Coinsurance | —/37.00/— |
| Humana Paid | — |

Jan. 21, 2005, claim 123456789012354
Respiratory care Group (In-network)
Respiratory Therapy,
Acute Respiratory
Total charge 150.00 PENDING
Awaiting benefit determination.

Jan. 21, 2005, Claim 123456789012356
Radiology Group of Louisville (In-network)
X-Ray Chest, Acute Respiratory

| | |
|---|---|
| Total Charge | 537.00 |
| Humana discounts | 100.00 |
| Humana exclusions | 124.00 |
| What you paid with this plan | |
| Copay/Deductible/Coinsurance | 40.00/273.00/— |
| Humana Paid | — |

We have received this claim and we are currently processing it. These processed claims show that this member has deductible totals of $902.80 and office copay totals of $65. These totals were shown on the previous page under "What you've spent". Underneath the claims detail, as this member has a claim for venous blood draw denied, the "!" marker can be provided with the following information: You have a denied claim. If you believe this claim should be fully or partially covered, you may appeal by writing to us within 180 days of the date that you receive the denial (unless your plan or any applicable state law allows you additional time). Mail your appeal to Grievance and Appeals, P.O. Box 14618, Lexington, Ky. 40512-4546.

It is noted that this list of claims pulls claims to all providers which currently are communicated by separate EOBs and consolidates and presents them to the member in a tight table. Pended/Denied markers may be included within the List of Claims and provide the Pended/Denied reason information in the same place as the paid claims detail, so that the member does not have to search on the back or bottom of the page for the Pended/Denied code detail. This page identifies the status of each claim. For claims which have been processed and paid by Humana, the claim and service are specifically identified, the total charges are shown, the Humana discount is identified, any member copay and deductible are identified and the amount paid by the member and Humana is identified. For claims pending or denied, the claim and service is again specifically identified and the total charge amount pending or denied shown. For denied claims, an explanation is provided. For claims pending, the current status of the pending claim is provided.

An example page 4 of 9 of the statement, which provides prescription claim information and communications to Humana by the member during the quarter this statement covers: Prescription claims we received (Jan. 1 to Mar. 31, 2005)

This list shows all of your submitted prescriptions and total costs covered by Humana for the last quarter. Adjusted claims may not be reflected in this display; or if displayed, the amount paid may differ due to the amount of the adjustment. You should always discuss prescription drugs with your doctor to determine appropriateness or clinical effectiveness.

As a Humana member, you have the advantage of a reduced price negotiated with Humana and the Pharmacy. The cost of the prescription displayed above is the plan price negotiated with the pharmacy at the time of purchase and does not take into account other reimbursements, including rebates. Retail prices can vary by pharmacy and location and by specific quantity, strength and/or dosage of the medication.

| Jan. 9, 2005 Wal-Mart Drug Name - Amoxicillin, 500 mg, 20 capsules | |
|---|---|
| Cost of Prescription | 11.66 |
| Humana Allowance | 30.00 |
| What you paid | — |
| What Humana paid | 11.66 |
| Amount deposited to Rx account | 18.34 |

| Jan. 9, 2005 Wal-Mart Drug Name - Protonix, 40 mg. 30 tables | |
|---|---|
| Cost of Prescription | 84.20 |
| Humana Allowance | 10.00 |
| What you paid | 74.20 |
| What Humana paid | 10.00 |
| Amount deposited to Rx account | — |

| Jan. 26, 2005 Walgreens Drug Name - Albuterol Inhalation, 90 mcg | |
|---|---|
| Cost of Prescription | 16.70 |
| Humana Allowance | 30.00 |
| What you paid | — |
| What Humana paid | 16.70 |
| Amount deposited to Rx account | 13.30 |

| Feb. 11, 2005 Wal-Mart Drug Name - Protonix, 40 mg, 30 tablets | |
|---|---|
| Cost of Prescription | 84.20 |
| Humana Allowance | 10.00 |
| What you paid | 74.20 |
| What Humana paid | 10.00 |
| Amount deposited to Rx account | — |

| Mar. 11, 2005 Wal-Mart Drug Name - Protonix, 40 mg. 30 tablets | |
|---|---|
| Cost of Prescription | 84.20 |
| Humana Allowance | 10.00 |
| What you paid | 74.20 |
| What Humana paid | 10.00 |
| Amount deposited to Rx account | — |

| Mar. 21, 2005 Mail Order Village Pharmacy Drug Name - Lotensin, 20 mg, 90 tablets | |
|---|---|
| Cost of Prescription | 106.47 |
| Humana Allowance | 60.00 |
| What you paid | 46.47 |
| What Humana paid | 60.00 |
| Amount deposited to Rx account | — |

After the prescription claim information, several markers can be included. For example, an "!" marker can state: Don't take more or less of your medication(s) than your doctor has prescribed. A "stethoscope" marker can provide: You may be able to save money each month on your prescription medication by taking a lower-cost generic that may provide the same treatment as the brand name. Visit www.humana.com or call Customer Service at 1-800-917-2807 to see if your prescription drugs have lower-cost generic alternatives. A "computer mouse" marker can provide: Did you know that you could use the Rx Calculator on MyHumana to find possible lower cost alternative to your current medications? You can register for MyHumana at www.humana.com.

These processed claims show that Humana has paid $118.36 and this member has paid $269.07 for these six prescription claims. These totals were shown on page 2 under "What you've spent".

Next on this page is the section reflecting the contact the member had with Humana during the statement quarter: Communications you made to Humana (Jan. 1 to Mar. 31, 2005) This list of inquiries is provided to help you manage service interactions and may include inquiries made on your behalf. Due to the fact that inquiries can be directed to different areas within Humana, this may not be a complete list. This list may include calls that are not yet resolved.

| Date you Called | Transaction Number | Type | Reason you called |
|---|---|---|---|
| Jan. 20, 2005 | 5614 | Phone | Question about a claim |
| Feb. 16, 2005 | 2478 | Phone | Question about authorization Options |
| Mar. 2, 2005 | 5682 | Phone | Question about your prescription benefits |

This communications section can be followed by a "computer mouse" marker, which provides: Register Now for MyHumana, your password-protected personal home page on www.humana.com. You can see your claims, benefit and prescription coverage information anytime. It's easier than ever to sign up for MyHumana, so register now!

An example page 5 of 9 of the statement, which provides plan year cumulative information on the members health care accounts, such as a flexible spending account:

Your health care accounts

Your Flexible Spending Account (FSA) summary (as of Mar. 31, 2005)

| | | |
|---|---|---|
| Amount you chose for you FSA | | $1,500.00 |
| Amount you've contributed to date | $750.00 | |
| Amount you've spent to date | | |
| First quarter | $945.07 | |
| Total spent | | $945.07 |
| Balance remaining in your FSA | | $554.93 |

In addition to providing these amounts, a graphical representation can be provided, such as an x-y graph with the four plan year quarters on the x-axis (March 31, June 30, September 30, and December 31) and the dollar amount on the y-axis. In this situation, since the member chose to contribute $1,500 for the plan year and has already spent $945.07 to leave a balance for the rest of the plan year of $554.93, a line would connect $1,500 at the y-axis with $554.93 at March 31 on the x-axis. Also, information that the member will find useful about the flexible spending account can be provided, such as: The IRS may request that you submit receipts to confirm that FSA, HAS and PCA funds were used for appropriate medical expenses. Please keep all receipts from these accounts for IRS substantiation. You may find the list below helpful when tracking expenses which need receipts. For questions regarding your FSA, HSA, or PCA account please call 1-800-604-6228. Next, FSA activity is detailed in a section entitled: Your Flexible Spending Account (FSA) activity (Jan. 1 to Mar. 31, 2005)

| Date posted | Name of provider or pharmacy | Type of transaction | Amount |
|---|---|---|---|
| Jan. 1, 2005 | Opening balance | | $1,500.00 |
| Jan. 5, 2005 | Carol Jones, MD | Reimbursement | 25.00 |
| Jan. 9, 2005 | Wal-Mart | Debit card | 74.20 |
| Feb. 11, 2005 | Wal-Mart | Debit card | 74.20 |
| Feb. 4, 2005 | St. Jude Hospital | Debit card | 611.00 |
| Mar. 9, 2005 | Radiology Group of Louisville | Debit card | 40.00 |
| Mar. 11, 2005 | Wal-Mart | Debit card | 74.20 |
| Mar. 21, 2005 | Mail Order Village Pharmacy | Reimbursement | 46.47 |
| Mar. 31, 2005 | Remaining Balance | | 554.93 |

Additional useful FSA information can be provided, such as a list of "What you can use your FSA to purchase"
Other members like you have used their FSA to:
    purchase prescription drugs or insulin
    birth control drugs (prescribed)
    wheelchairs
    crutches
    special mattresses to alleviate arthritis
    oxygen equipment to relieve breathing problems
    artificial limbs
    medically necessary support hose
    x-ray treatments
    treatment of alcoholism or drug dependency While this example shows information about a flexible spending account, additional account types may be represented, such as, for example, Health Savings Accounts, Health Care Accounts. These accounts may behave differently than a flexible spending account and would be represented differently. For example, Health Savings Accounts are considered cash accounts, and may be represented with varying labels or graphs. Below the account activity section may be an area to provide a specific message, coupon, article, or other communication type personalized to that member's profile, claims history, etc.

An example pages 6 and 7 of 9 of the statement, which provide information about: "What's new in health care?"

An example of this information, which is dynamic information which can relate specifically to this member, either based on member claims or member requests, and would change from statement to statement is:
We strive to personalize your health news by selecting articles about new research and studies that are relevant to your life. This information is in no way intended to interfere with the medical advice or recommendations of your doctor. Consult your doctor before making any change that could possibly affect your health.
Antibiotics Test May Soon be in U.S.

A simple blood test can help determine which patients require antibiotics and which won't benefit from the medication.

A Swiss study published in 2004 showed that the test for a protein called procalcitonin halved the number of antibiotic prescriptions given to people with lung infections without hurting overall care.

A version of the procalcitonin test is already available in Europe but it hasn't yet been approved for use in the United States. A review by a protocol committee from the U.S. Food and Drug Administration in March 2005 was favorable, but the FDA hadn't approved the test as of July 2005.

The test's developers estimate it would cost between $30 and $50, although experts say it more than pays for itself by reducing the unnecessary use of antibiotics. While overuse of antibiotics typically isn't harmful to individual patients, the practice is blamed for the alarming rise in drug-resistant bacteria. Dr. Stuart Levy, a Tufts University professor and president of the Alliance for the Prudent Use of Antibiotics, said "to have a test like this would in principle be a boon, because if we know that it's viral and not bacterial," doctors could avoid prescribing antibiotics that wouldn't work anyway. The biggest impact of such a test—whether for procalcitonin or another infection indicator—would be in stopping unnecessary antibiotic therapy in the community, where the bulk of misuse occurs, Levy added.

Even if doctors in the United States were to adopt a procalcitonin test as they have in Europe, Scott Hanes, a pharmacology researcher at the University of Illinois at Chicago, predicted that it would supplement other tools for identifying the causes of infections. These include blood tests for other signals of inflammation, including C-reactive protein, lactate and interleukin (IL)-6, as well as physical exams such as bronchoscopy, in the case of pneumonia.

"It's not going to be relied upon as the sole tool to determine if you're going to receive antibiotics," he said.

SOURCES: Stuart Levy, M.D., professor, Molecular Biology and Microbiology, Tufts University School of Medicine and president, Alliance for the Prudent Use of Antibiotics; pharmacology researcher at the University of Illinois, Chicago. Copyright© 2005 www.healthday.com. ScoutNews, LLC. All rights reserved.
Online Guide for Prescription Drug Comparisons Launched The popular magazine Consumer Reports has developed a Web site which offers consumers the opportunity to compare the prices and effectiveness of common medications. The publication has launched an educational and outreach initiative which includes a free Web site, www.crbestbuydrugs.org, that will compare drugs in terms of price, effectiveness and safety. One drug in each of several categories will earn a "Best Buy" distinction.

"We know that consumers are very concerned and confused about finding prescription drugs that are proven to be safe and effective and that they can afford," said Joel Gurin, executive vice president of Consumers Union, which publishes Consumer Reports. "We asked ourselves, 'What if we can do for drugs what we do for cars and cameras?'"

"Millions of Americans cannot afford the medications they need," added Dr. George Benjamin, executive director of the American Public Health Association. The situation is worse for elderly people, who generally need more medications and have fewer financial resources, Benjamin said. According to Gurin, the Best Buy tool will enable consumers to save as much as $2,000 per year without sacrificing quality of treatment or safety.

The initiative takes its drug effectiveness information from the Drug Effectiveness Review Project (DERP), which is now used in a dozen states. "DERP looks at all of the credible studies that have been done worldwide, and their process is just impeccable," said Consumers Union health policy director Gail Shearer. "It's highly peer-reviewed and totally transparent." Consumer Reports provides additional data and analysis. Price information is based on average retail prices paid in cash by consumers at pharmacies, and will be monitored monthly.

The Best Buy project is kicking off with three drug categories—cholesterol-lowering statins, proton pump inhibitors for heartburn and acid reflux, and nonsteroidal anti-inflammatory drugs (NSAIDs) for arthritis and pain—and will be adding more each month until it has 20 categories.

CDC Study Finds Americans Taking More Prescription Medications

Just over 44 percent of Americans use at least one prescription drug, and nearly 17 percent take at least three, according to a U.S. Centers for Disease Control and Prevention survey.

Five out of six persons 65 and older are taking at least one medication, and almost half the elderly take three or more, according to the agency's annual report on the nation's health.

The use of antidepressants among adults almost tripled between 1988-1994 and 1999-2000, with 10 percent of women 18 and older and 4 percent of men now taking the drugs. Prescriptions for nonsteroidal anti-inflammatory drugs, antidepressants, blood glucose/sugar regulators, and cholesterol-lowering statin drugs, in particular, were also on the rise.

Prescription drugs, which now account for about one-tenth of the nation's total healthcare bill, are the fastest growing expenditure, the report said. Spending on prescription drugs has risen at least 15 percent every year since 1998.

The wide-ranging report on the state of America's health also found that:

Americans' life expectancy rose to 77.3 years in 2002, a record.

Deaths from the top three killers—heart disease, cancer, and stroke—fell by 1 percent to 3 percent from the prior survey.

Overall health care spending climbed 9.3 percent in 2002 to $1.6 trillion.

SOURCE: National Vital Statistics Reports, Vol. 53, No. 6, U.S. Centers for Disease Control and Prevention, November, 2004 Copyright© 2005 www.healthday.com. ScoutNews, LLC. All rights reserved.

For this health care news and information, articles included on new developments and trends can be triggered by demographics, claims data or custom options to present content on disease conditions that are of particular relevance or interest to that member. For most, there is an overwhelming amount of information available through various Internet search sites or in magazines and other printed publications. This section's purpose is to provide a manageable amount of good information about topics of interest so that the member can stay current with what they should be paying attention to if they want to improve their health or maintain their already good health. This section can be personalized to provide information on topics specifically identified by the member as being of interest or, if no member interests are identified, personalized by Humana based on this member's claim or other history, or non-personalized general health care news. For example, the humana.com website will include a listing of topics and conditions that will interest different members. Each member can select from this listing of topics and conditions to receive information of highest interest to that member. This information may be generated by Humana or may come from external sources.

Following the "What's new in healthcare section", because there is room on this page, a privacy section can be provided as well as one or more coupons specifically relevant for this member. With a "lock" marker, we can have a section titled "Your privacy is important to us", reading: Your privacy is important to Humana. At Humana, we consider your personal, health and financial information to be confidential. Humana protects your information and only uses or discloses your information in accordance with federal and state privacy laws and Humana's privacy policy. For additional information on Humana's privacy policy, please access Humana's Notice of Privacy Practices on the Web at www.humana.com.

As there is additional room on this page, one or more manufacturer's coupon for a discount for a drug this member would likely use can be provided. If there is not room on this page, any coupon can be omitted or included elsewhere in the statement.

An example page 8 of 9 of the statement, which shows the member's personal health care record over a twelve month rolling period is provided. This personal health record compiles twelve months of health care services, integrating medical and pharmacy in one linear chronological view that includes medical information like procedure, physician specialty and other information not previously available with claims in EOBs. The information presented is extracted from both the member medical and pharmacy claim information and currently shows by date the provider and activity/procedure/test, any diagnosis made by the provider, and any medication prescribed and the dosage. Here, as this statement ends Mar. 31, 2005, the record will show the period of Apr. 1, 2005-Mar. 31, 2005, as follows:

Your personal health care record (Apr. 1, 2004 to Mar. 31, 2005)

Your personal healthcare record is provided as a courtesy to help you manage your interactions with health care providers such as doctors and hospitals. You may want to take this with you to your next appointment to give your doctor a broader view of your healthcare interactions This list is compiled from information submitted with claims to your insurance plan. There may be information shown here that is incomplete from a medical perspective. Where this list differs from information you received from your doctor concerning a surgery or procedure, for example, please check with your doctor for the correct information. This list is not intended as a substitute for a medical record.

| Date | Name of Provider, Specialty | Procedure | Name of Drug and Dosage |
|---|---|---|---|
| Apr 15, 2004 | Carol Jones, MD Allergist | Allergy shots | |
| Apr 20, 2004 | Mail Order Village Pharmacy | | Lipitor 20 mg, 90 |
| Apr. 22, 2004 | Carol Jones, MD Allergist | Allergy shots | |
| May 3, 2004 | James Dean, MD Gastroenterology | Colonsigmoidoscopy | |
| May 22, 2004 | Steven Smith, MD, Internal Medicine | Pulmonary function test | |
| May 22, 2004 | Labcorp of America Holdings | Venipuncture | |
| May 26, 2004 | Walgreens | | Albuterol Inhalation, 90 mcg |
| Jun. 26, 2004 | Mail Order Village Pharmacy | | Lipitor, 20 mg, 90 |
| Aug. 15, 2004 | Carol Jones, MD, Allergist | Allergy shots | |
| Sept. 20, 2004 | Mail Order Village Pharmacy | | Lipitor, 20 mg, 90 |
| Oct. 15, 2004 | Carol Jones, MD, Allergist | Allergy shots | |
| Nov. 9, 2004 | James Dean, MD, Gastroenterology | Colonsigmoidoscopy | |
| Nov. 10, 2004 | Wal-Mart | | Protonix, 40 mg, 30 |
| Dec. 11. 2004 | Wal-Mart | | Protonix, 40 mg, 30 |
| Dec. 20, 2004 | Mail Order Village Pharmacy | | Lipitor, 20 mg, 90 |
| Jan. 5, 2005 | Carol Jones, MD, Allergist | Screening Infection | |

| Date | Name of Provider, Specialty | Procedure | Name of Drug and Dosage |
|---|---|---|---|
| Jan. 9, 2005 | Wal-Mart | | Amoxicillin, 500 mg, 14 |
| Jan. 9, 2005 | Wal-Mart | | Protonix, 40 mg, 30 |
| Jan. 19, 2005 | Jefferson County, Ambulance | Transport | |
| Jan. 19, 2005 | St. Jude Hospital | Emergency Room | |
| Jan. 20, 2005 | St. Jude Hospital | Inpatient Bed Stay | |
| Jan. 20, 2005 | St. Jude Hospital | Venous Blood Draw | |
| Jan. 20, 2005 | St. Jude Hospital | Injection | |
| Jan. 21, 2005 | Respiratory Care Group | Acute Respiratory | |
| Jan. 21, 2005 | Radiology Group of Louisville | X-Ray Chest | |
| Jan. 26, 2005 | Walgreens | | Albuterol Inhalation, 90 mcg |
| Feb. 11, 2005 | Wal-Mart | | Protonix, 40 mg, 30 |
| Mar. 9, 2005 | Wal-Mart | | Protonix, 40 mg, 30 |
| Mar. 21, 2005 | Mail Order Village Pharmacy | | Lotensin, 20 mg, 90 |

Following the personal health care record, based upon the drugs this member is taking or the procedures this member has had, a "stethoscope" marker can be provided to give the member useful information. An example would be: According to the National Heart, Lung and Blood Institute, cholesterol levels and certain other lab tests such as liver function tests should be measured at last annually or as determined by your doctor.

An example page 9 of 9 of the statement provides the member with a record of prescriptions filled by that member over a year period. The list of medications compiles all the prescription medications a member has used in the past twelve months and lists them together, to provide a portable record the member can show their physician instead of taking in all their medications. The prescription record identifies prescribed medications from the pharmacy claim database. Identified are the name of the drug, the quantity, the dosage, the days supply, the number of times the member has filled or refilled the prescription, and the doctor and his or her specialty who wrote the prescription. As with the personal health care record, this example record covers the period Apr. 1, 2004-Mar. 31, 2005, as follows:

A record of your prescriptions (Apr. 1, 2004 to Mar. 31, 2005) You should always discuss prescription drugs with your doctor to determine appropriateness or clinical effectiveness.

| | |
|---|---|
| Name of drug, dosage | Albuterol inhalation, 90 mcg |
| Quantity | 1 |
| Days supply | As needed |
| Number of times filled/refilled | 2 |
| Doctor who prescribed drug/Specialty | Steven Smith, MD |
| Name of drug, dosage | Amoxicillin capsules, 500 mg |
| Quantity | 30 |
| Days supply | 15 |
| Number of times filled/refilled | 1 |
| Doctor who prescribed drug/Specialty | Carol Jones, MD |
| Name of drug, dosage | Lotensin tablets, 20 mg |
| Quantity | 90 |
| Days supply | 90 |
| Number of times filled/refilled | 1 |
| Doctor who prescribed drug/Specialty | Steven Smith, MD |
| Name of drug, dosage | Lipitor tablets, 20 mg |
| Quantity | 90 |
| Days supply | 90 |
| Number of times filled/refilled | 4 |
| Doctor who prescribed drug/Specialty | Steven Smith, MD |
| Name of drug, dosage | Protonix tablets, 40 mg |
| Quantity | 30 |
| Days supply | 30 |
| Number of times filled/refilled | 5 |
| Doctor who prescribed drug/Specialty | James Dean, MD |

Following the prescription record, an appropriate marker can be used to bring additional related information to the member. For example, a "computer mouse" marker can be presented with the following information: You can visit www.humana.com and use the Drug Coverage Search to determine whether a specific prescription drug is covered by your Humana plan. You can also check for quantity, dosage strength, side effects, and other drug-specific information. Humana's drug list is the most up-to-date list of prescription medications approved for coverage.

While an example statement has been explained, from the medical, pharmacy, dental, and other claim information, additional information can be provided to each member which has not been mentioned so far, particularly where the member has provided other health related information about themselves. For example, the member may complete a health risk assessment questionnaire. This could be completed on paper or electronically at the myhumana.com website. With the historical claims information for a member and the member provided additional health information, a health wellness evaluation can be completed. This evaluation can produce a health wellness score which can then be used for identifying future health risk and may be used for other health initiatives. For example, the "Your eligible programs" section on page 2 identified the Humana Personal Nurse, Disease Management, Health Risk Assessment, Non-smoking Benefit, and Wellness Points Programs as possible programs. From the member provided health information and the calculated health wellness score, a direct targeted communication may be sent to the member providing information on a specific program and possibly inviting the member to join that program. Also, based on the member provided health information and the calculated health wellness score, Humana may select content to include in the "what's new in health care" section described above in the description of pages 6 and 7 of the example statement.

By providing the individual member with a statement, such as has been described herein and which provides extensive information on that member's health care experiences and information which is tailored to that member's interests and possibly based on that member's claim history, the health care consumer will be a better educated consumer of health care services able to make more informed decisions.

For members enrolled in prescription plans only, similar statements are provided, with the appropriate information extracted from the ODS 50 and the statement again provided in print or electronically. Naturally, this statement will only include prescription claim and plan information.

The member's personal prescription benefits statement will, as with the health finance and benefits statement, include member and statement information; a "What's inside" table of contents section; an identification of the markers, for example as seen in FIG. 2; a "Numbers for you to watch" section, which, at a glance, shows the member where they stand in the prescription plan program; and a numerical and bar graph representation showing the member what their prescription costs are to date in the plan year, what the plan paid, and what the member paid.

Further, as with the health statement, the individual prescription claims are detailed with the drug name, the date and who filled the prescription, what the prescription cost, what the member paid, and what the plan paid. Markers are used in this section, as well as throughout the statement to bring information to the member's attention. For example, an "!" marker could point out to the member that a drug is going to change drug categories and will affect future member costs. A "$" savings alert marker could identify generic alternatives to brand name drugs the member has purchased. A "computer mouse" on-line resources marker could point the member to the on-line RxCalculator tool.

Again, as in the health statement, a "What's new in healthcare" section can be provided to bring information to the member. This information can be general in nature, be information on a topic specifically requested by the member, and/or be information the statement prepared believes will be useful to the member based on that specific member's prescription claims history.

The foregoing detailed description is given primarily for clearness of understanding and no unnecessary limitations are to be understood therefrom for modifications can be made by those skilled in the art upon reading this disclosure and may be made without departing from the spirit of the invention.

What is claimed is:

1. A method of providing to a plan member enhanced healthcare, finance and benefit information via a personal health finance and benefits statement, the method comprising the following steps:
   a) providing an operation data storage maintaining data on at least one plan member; on that at least one plan member's benefits; on information regarding a medical category identified as of interest to that at least one plan member; and on that at least one plan member's medical claim data, prescription claim data, health-related account data, and disease management program data, wherein maintaining data on information regarding a medical category identified as of interest to said at least one plan member includes identifying as a medical category as of interest to said at least one plan member by a process of identification comprising the following steps:
      (1) determining if said at least one plan member has identified a medical category as being of interest;
         (a) if so, identifying said medical category identified by said at least one plan member as a medical category identified as of interest to that said at least one plan member, and proceeding to step b);
         (b) if not, proceeding to step a)(2);
      (2) determining if a statement provider has identified a medical category as being of interest to that said at least one plan member based on at least one of: said at least one plan member's claims history, health information provided by said at least one plan member, and a calculated health wellness score;
         (a) if so, identifying said medical category identified by said statement provider as a medical category identified as of interest to that said at least one plan member, and proceeding to step b);
         (b) if not, identifying general healthcare news as being of interest to that said at least one plan member;
   b) extracting from said data maintained information needed to produce a personal health finance and benefits statement for at least one plan member;
   c) creating additional data elements relevant to said at least one plan member by applying business rules and calculations to said extracted information;
   d) providing at least one statement template;
   e) using a composition engine, said composition engine receiving said extracted information, said additional data elements, and one of said at least one statement template as inputs, to create a completed statement for each of said at least one plan member for which information was extracted:
      (1) inserting said extracted information appropriately into said statement template to reflect to that said at least one plan member:
         (a) numbers for that said at least one plan member to watch which shows that member their plan year to date cost information in both a numerical and a graphical format;
         (b) personal profile information about that said at least one plan member and that said at least one plan member's plan including, in numerical and graphical format, any medical year to date co-payments for that member, any medical year to date in-network charges for that member; any medical year to date out-of-network charges for that member, any prescription year to date charges for that member;
         (c) information about each of that said at least one plan member's medical claims processed during at least a period of time covered by the statement, including resolution of each claim, what that said at least one plan member paid for each allowed claim, and what that said at least one plan member's plan paid for each allowed claim;
         (d) information about each of that said at least one plan member's prescription claims processed during at least said period of time covered by the statement, including resolution of each claim, what that said at least one plan member paid for each allowed claim, and what that said at least one plan member's plan paid for each allowed claim;
      (2) inserting into said statement template at least one pictorial marker with associated information related to said inserted extracted information to highlight that associated information to that said at least one plan member;
      (3) inserting into said statement template a list of any communication that said at least one plan member had with the plan provider;
      (4) inserting into said statement template any health-related account information for that said at least one plan member, including in numerical and graphical format account expenditure and balance information and including a list of any individual account activity plan year to date;
      (5) inserting into said statement template healthcare information relevant to that said at least one plan member, including said information regarding a medical category identified as of interest to said at least one plan member; and,
   f) providing that said at least one plan member with their completed statement.

2. The method of claim 1, where said at least one pictorial marker includes at least one of a savings alert marker, a health alerts marker, a plan alert marker, a personalization marker, an online resources marker, and a phone resources marker.

3. The method of claim 1, where the step of utilizing one of at least one statement templates to complete a statement for each of said at least one plan member for which information was extracted includes: inserting into said statement template a personal healthcare record for that said at least one plan member, the personal healthcare record including for a preceding year period a list, by date and provider, of any procedure provided or any drug and its dosage and quantity prescribed, and a list, by drug and dosage and quantity, of a number of times each drug was filled and the drug prescriber.

4. The method of claim 3, where said at least one pictorial marker includes at least one of a savings alert marker, a health alerts marker, a plan alert marker, a personalization marker, an online resources marker, and a phone resources marker.

5. The method of claim 1, where said healthcare information relevant to that said at least one plan member inserted into said statement template includes information based on that said at least one plan member's claims history.

6. The method of claim 5, where said healthcare information relevant to that said at least one plan member inserted into said statement template includes at least one coupon.

7. The method of claim 1, where said healthcare information relevant to that said at least one plan member inserted into said statement template includes information on topics requested by that said at least one plan member.

8. The method of claim 1, where the step of providing that said at least one plan member with their completed statement is accomplished electronically.

9. The method of claim 8, where that said at least one plan member views their completed statement via a member portal on the Internet.

10. The method of claim 9, where that said at least one plan member is notified by electronic mail that their completed statement is available for viewing at said member portal.

11. The method of claim 1, where the step of providing that said at least one plan member with their completed statement is accomplished by printing the statement and mailing it to that said at least one plan member.

\* \* \* \* \*